United States Patent
Gross et al.

(10) Patent No.: US 8,788,045 B2
(45) Date of Patent: Jul. 22, 2014

(54) TIBIAL NERVE STIMULATION

(75) Inventors: Yossi Gross, Moshav Mazor (IL); Noam Kinrot, Nesher (IL)

(73) Assignee: Bluewind Medical Ltd., Herzeliya (IL)

( * ) Notice: Subject to any disclaimer, the term of this patent is extended or adjusted under 35 U.S.C. 154(b) by 0 days.

(21) Appl. No.: 12/796,102

(22) Filed: Jun. 8, 2010

(65) Prior Publication Data
US 2011/0301670 A1 Dec. 8, 2011

(51) Int. Cl.
| A61N 1/08 | (2006.01) |
| A61N 1/36 | (2006.01) |
| A61N 1/372 | (2006.01) |
| A61N 1/05 | (2006.01) |
| A61N 1/375 | (2006.01) |

(52) U.S. Cl.
CPC ............ *A61N 1/372* (2013.01); *A61N 1/37205* (2013.01); *A61N 1/36157* (2013.01); *A61N 1/36071* (2013.01); *A61N 1/0558* (2013.01); *A61N 1/36171* (2013.01); *A61N 1/3756* (2013.01)
USPC .............................................. 607/46; 607/49

(58) Field of Classification Search
USPC .................................................... 607/46, 49
See application file for complete search history.

(56) References Cited

U.S. PATENT DOCUMENTS

| 6,272,383 | B1 | 8/2001 | Grey et al. |
| 6,292,703 | B1 | 9/2001 | Meier et al. |
| 6,735,474 | B1 * | 5/2004 | Loeb et al. ...................... 607/41 |
| 6,829,508 | B2 | 12/2004 | Schulman et al. |
| 6,909,917 | B2 | 6/2005 | Woods et al. |
| 7,027,860 | B2 | 4/2006 | Bruninga et al. |
| 7,177,698 | B2 | 2/2007 | Klosterman et al. |
| 7,324,852 | B2 | 1/2008 | Barolat et al. |
| 7,536,226 | B2 | 5/2009 | Williams et al. |
| 7,630,771 | B2 | 12/2009 | Cauller |
| 7,848,818 | B2 | 12/2010 | Barolat et al. |
| 7,974,706 | B2 | 7/2011 | Moffitt et al. |
| 7,996,089 | B2 | 8/2011 | Haugland et al. |
| 7,996,092 | B2 | 8/2011 | Mrva et al. |
| 8,019,443 | B2 | 9/2011 | Scheicher et al. |
| 8,131,377 | B2 | 3/2012 | Shhi et al. |
| 8,185,207 | B2 | 5/2012 | Molnar et al. |
| 2004/0015205 | A1 * | 1/2004 | Whitehurst et al. ............ 607/48 |
| 2004/0073270 | A1 | 4/2004 | Firlik et al. |
| 2004/0254624 | A1 | 12/2004 | Johnson |
| 2005/0143789 | A1 * | 6/2005 | Whitehurst et al. ............ 607/46 |
| 2006/0155345 | A1 | 7/2006 | Williams et al. |
| 2006/0271137 | A1 | 11/2006 | Stanton-Hicks |
| 2008/0027513 | A1 | 1/2008 | Carbunaru |
| 2008/0039915 | A1 | 2/2008 | Van Den Biggelaar et al. |
| 2009/0012590 | A1 | 1/2009 | Inman et al. |

(Continued)

OTHER PUBLICATIONS

C. Seper, "Neuros Medical Launches to Develop New Device to Block Amputee, Chronic Pain," Mar. 2009, 6 pages.

(Continued)

*Primary Examiner* — Alyssa M Alter
(74) *Attorney, Agent, or Firm* — Symbus Law Group, LLC; Clifford D. Hyra

(57) ABSTRACT

Apparatus and methods are described, including identifying a subject as suffering from polyneuropathy. In response to the identifying, electrodes are placed within 1 mm of a tibial nerve of the subject, the electrodes being disposed on a housing that is at least partially flexible. The electrodes are driven to treat the polyneuropathy by driving a current into the tibial nerve. Other embodiments are also described.

30 Claims, 6 Drawing Sheets

(56) References Cited

U.S. PATENT DOCUMENTS

| | | |
|---|---|---|
| 2009/0281594 A1 | 11/2009 | King et al. |
| 2010/0121405 A1 | 5/2010 | Ternes et al. |
| 2010/0198298 A1 | 8/2010 | Glukovsky et al. |
| 2010/0241195 A1 | 9/2010 | Meadows et al. |
| 2010/0312320 A1 | 12/2010 | Faltys et al. |
| 2011/0046696 A1 | 2/2011 | Barolat et al. |
| 2011/0137365 A1 | 6/2011 | Ben-Ezra et al. |
| 2011/0160798 A1 | 6/2011 | Ackermann et al. |
| 2011/0208271 A1 | 8/2011 | Dobak |
| 2011/0224744 A1 | 9/2011 | Moffitt et al. |
| 2011/0282412 A1 | 11/2011 | Glukhovsky et al. |
| 2012/0041511 A1 | 2/2012 | Lee |
| 2012/0065701 A1 | 3/2012 | Cauller |
| 2012/0083857 A1 | 4/2012 | Bradley et al. |
| 2012/0130448 A1 | 5/2012 | Woods et al. |
| 2012/0130463 A1 | 5/2012 | Ben-David et al. |

OTHER PUBLICATIONS

Urgent® PC, Simple. Safe. Effective. Neuromodulation System, Uroplasty Mar. 2009, 3 pages.

"JumpStart and Case Technology Ventures Invest in Neuros Medical," CTV Case Technology Ventures, Mar. 2009, 3 pages.

P.J. Theuvenet, et al., "Responses to Median and Tibial Nerve Stimulation in Patients with Chronic Neuropathic Pain," Brain Topography, 1999, pp. 305-313, vol. 11, No. 4, an Abstract, 1 page.

D.G. Armstrong, et al., "Is Electrical Stimulation Effective in Reducing Neuropathic Pain in Patients with Diabetes," J. Foot Ankle Surg., Jul.-Aug. 1997, vol. 36, No. 4, an Abstract, 1 page.

Office Action received in U.S. Appl. No. 13/528,433, dated Dec. 5, 2013.

\* cited by examiner

FIG. 3A
FIG. 3B
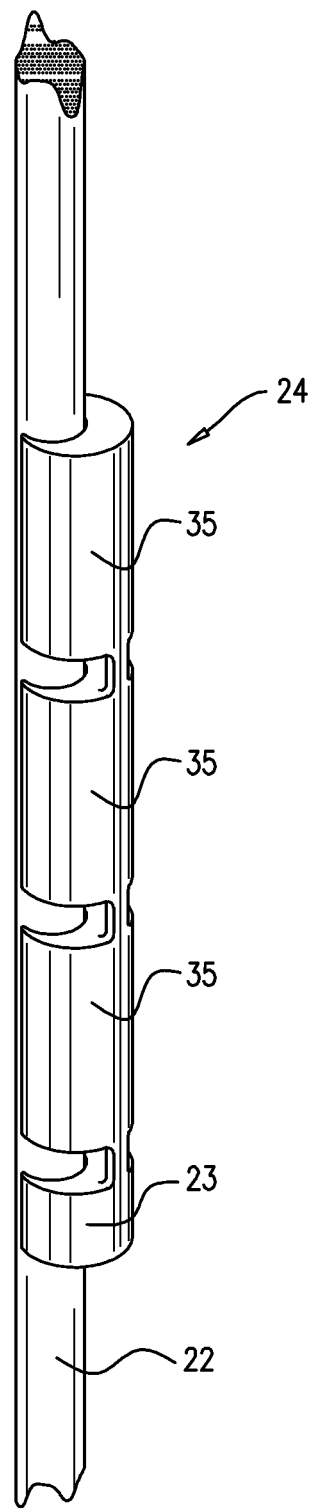
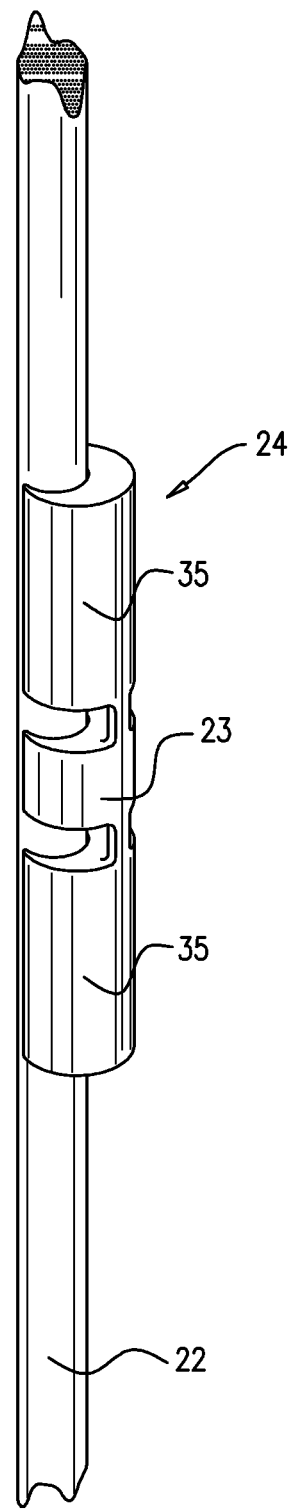

TIBIAL NERVE STIMULATION

FIELD OF EMBODIMENTS OF THE INVENTION

Some applications of the present invention generally relate to medical apparatus. Specifically, some applications of the present invention relate to stimulation of the tibial nerve.

BACKGROUND

Polyneuropathy is a disease of the peripheral nerves. Typically, patients suffering from polyneuropathy experience chronic pain. In many cases polyneuropathy is a symptom of diabetes mellitus.

The tibial nerve is a branch of the sciatic nerve that passes alongside the tibia and into the foot. At the ankle, the tibial nerve is relatively close to the surface of the skin. In percutaneous tibial nerve stimulation, a percutaneous electrode is inserted into the subject's ankle, and the tibial nerve is stimulated, for example, in order to treat pelvic pain and/or incontinence.

U.S. Pat. No. 6,735,474 to Loeb describes a method and system for treatment of incontinence and/or pelvic pain including the injection or laparoscopic implantation of one or more battery- or radiofrequency-powered microstimulators beneath the skin of the perineum and/or adjacent the tibial nerve. The devices are described as being programmed using radio-frequency control via an external controller that can be used by a physician to produce patterns of output stimulation pulses judged to be efficacious by appropriate clinical testing to diminish symptoms. The stimulation program is described as being retained in the microstimulator device or external controller and as being transmitted when commanded to start and stop by a signal from the patient or caregiver. The system and method are described as reducing the incidence of unintentional episodes of bladder emptying by stimulating nerve pathways that diminish involuntary bladder contractions, improving closure of the bladder outlet, and/or improving the long-term health of the urinary system by increasing bladder capacity and period between emptying. The incidence of fecal incontinence is described as being similarly reduced or eliminated. Furthermore, the system and method are described as reducing or eliminating the incidence of pelvic pain by chronically stimulating nerve pathways that derive from the sacral roots using a miniature implantable neurostimulator that can be implanted with a minimal surgical procedure. The system and method are described as allowing a patient to be taught to receive one or more patterns of neural stimulation that can be prescribed by a physician and administered without continuous oversight by a clinical practitioner.

Neuros Medical (Ohio, USA) manufactures a system that is described as delivering high-frequency stimulation to sensory nerves in the peripheral nervous system to block chronic pain. The system consists of an electrode (also known as a lead) placed around a peripheral nerve and powered by a pace-maker size generator that is implanted into the chest cavity, abdomen, or lower leg. In a press release, dated Mar. 17, 2009 it was stated that the generator operates in a much higher frequency range than conventional neurostimulation devices, and, therefore, the technology is able to stop nerve activity to block pain completely, as opposed to simply masking the pain signal.

Uroplasty Inc. (Minnesota, USA) manufactures the Urgent® PC Neuromodulation System, which is described as using percutaneous tibial nerve stimulation (PINS) for treating urinary urgency, urinary frequency, and urge incontinence.

The following references may be of interest:
U.S. Pat. No. 7,536,226 to Williams
U.S. Pat. No. 6,829,508 to Schulman
U.S. Pat. No. 6,272,383 to Grey
US 2008/0039915 to Van Den Biggelaar
US 2006/0271137 to Stanton-Hicks
US 2006/0155345 to Williams
US 2005/0143789 to Whitehurst
US 2004/0254624 to Johnson
"Is electrical stimulation effective in reducing neuropathic pain in patients with diabetes?" by Armstrong, J Foot Ankle Surg. 1997 July-August; 36(4):260-3
"Responses to Median and Tibial Nerve Stimulation in Patients with Chronic Neuropathic Pain," by Theuvenet, Brain Topography, Volume 11, Number 4, 1999, pp. 305-313(9)

SUMMARY OF EMBODIMENTS

For some applications of the present invention, a subject is identified as suffering from polyneuropathy. Electrodes are disposed on a housing that is at least partially flexible. The electrodes are placed in contact with the subject's tibial nerve. The polyneuropathy is treated by driving a current into the tibial nerve, via the electrodes. Typically, the housing is such that it maintains contact between the electrodes and the tibial nerve. A control unit that is typically disposed outside of the subject's body drives the electrodes. For example, the control unit may be coupled to a sock that is worn by the subject.

There is therefore provided, in accordance with some applications of the present invention, a method, including:
 identifying a subject as suffering from polyneuropathy; and
 in response to the identifying:
  placing electrodes within 1 mm of a tibial nerve of the subject, the electrodes being disposed on a housing that is at least partially flexible; and
  driving the electrodes to treat the polyneuropathy by driving a current into the tibial nerve.

For some applications, placing the electrodes includes:
 when the electrodes are driven to drive the current into the tibial nerve,
 reducing a current path from the electrodes away from the tibial nerve, using the housing, by
 placing the electrodes within 1 mm of the tibial nerve, in a given configuration with respect to the housing.

For some applications, the method further includes detecting a myographic signal of the subject, and driving the electrodes includes driving the electrodes responsively to the myographic signal.

For some applications, the housing includes flexible and rigid portions thereof, the portions being articulatably coupled to each other, and placing the electrodes within 1 mm of the tibial nerve includes placing the electrodes within 1 mm of the tibial nerve of the subject, the electrodes being disposed on the housing that includes the flexible and the rigid portions thereof.

For some applications, the method further includes, subsequent to placing the electrodes within 1 mm of the tibial nerve of the subject, coupling the housing to the tibial nerve by changing a shape of the housing.

For some applications, placing the electrodes within 1 mm of the tibial nerve of the subject includes placing the electrodes in contact with the tibial nerve.

For some applications, placing electrodes within 1 mm of the tibial nerve of the subject includes injecting the housing into the subject's ankle.

For some applications, driving the electrodes to drive the current includes driving the electrodes to drive a current having an amplitude of up to 10 mA.

For some applications, placing the electrodes includes placing the electrodes within 0.5 mm of the tibial nerve.

For some applications, placing the electrodes includes placing the electrodes within 0.3 mm of the tibial nerve.

For some applications, driving the electrodes includes driving the electrodes from outside a body of the subject.

For some applications, driving the electrodes from outside the subject's body includes driving the electrodes using a control unit that is coupled to an element that is coupled to the subject's ankle.

For some applications, driving the electrodes to drive the current includes driving the electrodes to drive a current having a frequency of 20 Hz to 100 Hz.

For some applications, driving the electrodes to drive the current includes driving the electrodes to drive a current having a frequency of 40 Hz to 60 Hz.

For some applications, driving the electrodes to drive the current includes driving the electrodes to drive the current for a therapy period having a duration of between two minutes and ten minutes.

For some applications, driving the electrodes to drive the current for the therapy period includes driving the electrodes to drive the current during 2-8 therapy periods per day.

For some applications, driving the electrodes to drive the current for the therapy period includes driving the electrodes to drive the current during 2-8 therapy periods per week.

For some applications, driving the electrodes to drive the current includes driving the electrodes to drive a current having an amplitude of between 0.2 mA and 8 mA.

For some applications, driving the electrodes to drive the current includes driving the electrodes to drive a current having an amplitude of between 0.5 mA and 4 mA.

For some applications, placing electrodes within 1 mm of the tibial nerve of the subject includes inserting the electrodes into the tibial nerve.

For some applications, inserting the electrodes into the tibial nerve includes expanding a spring, the electrodes being coupled to the spring.

For some applications, inserting the electrodes into the tibial nerve includes positioning the electrodes adjacent to the tibial nerve by moving the housing alongside the tibial nerve in a first direction, and, subsequently, inserting the electrodes into the tibial nerve by moving the housing in a second direction, the second direction being opposite to the first direction.

For some applications, placing the electrodes within 1 mm of the tibial nerve of the subject includes coupling the housing to the tibial nerve via one or more coupling elements that are coupled to the housing.

For some applications, coupling the housing to the tibial nerve via the one or more coupling elements includes coupling the housing to the tibial nerve via one or more spiral coupling elements.

There is further provided, in accordance with some applications of the present invention, apparatus for treating polyneuropathy of a subject, including:

one or more electrodes configured to be placed in contact with a portion of the subject's body within 1 mm of a tibial nerve of the subject;

a housing that is at least partially flexible configured to support the electrodes and to maintain contact between the electrodes and the portion by bending; and a control unit configured to be placed outside a body of the subject, and to drive the electrodes to treat the polyneuropathy by driving a current into the tibial nerve.

For some applications, the housing includes a shape-change material, and the housing is configured to maintain contact between the electrodes and the portion by changing a shape of the housing.

For some applications, the housing is configured to reduce a current path from the electrodes away from the tibial nerve.

For some applications, the control unit includes a myographic sensor configured to detect a myographic signal of the subject, and the control unit is configured to drive the electrodes responsively to the myographic signal.

For some applications, the housing includes flexible and rigid portions thereof, the portions being articulatably coupled to each other.

For some applications, the apparatus further includes an implantable control component configured to receive a signal from the first control unit, the implantable control component is disposed within the rigid portion of the housing, and the electrodes are disposed within the flexible portion of the housing.

For some applications, the apparatus further includes a sock that is configured to be worn on a foot of the subject, and the control unit is coupled to the sock.

For some applications, the apparatus further includes an introducer, and the electrodes are configured to be placed in contact with the subject's tibial nerve by the housing being injected to a vicinity of the tibial nerve via the introducer.

For some applications, the apparatus further includes coupling elements that are coupled to the housing and that are configured to automatically couple the housing to the tibial nerve by automatically becoming anchored to tissue in the vicinity of the tibial nerve.

For some applications, the coupling elements include spiral coupling elements.

For some applications, the introducer and the housing are shaped such that a rotational position of the electrodes is fixed with respect to the introducer during injection of the housing via the introducer.

For some applications, the housing has a non-circular cross-section and the introducer is shaped to define a lumen that has a non-circular cross-section that corresponds to the cross-section of the housing.

For some applications, the housing is shaped to define a protrusion and the introducer is shaped to define a groove that corresponds to the protrusion.

For some applications, the housing is shaped to define a groove and the introducer is shaped to define a protrusion that corresponds to the groove.

The present invention will be more fully understood from the following detailed description of embodiments thereof, taken together with the drawings, in which:

BRIEF DESCRIPTION OF THE DRAWINGS

FIGS. 3A-B are schematic illustrations of housings having rigid and flexible portions thereof, in accordance with some applications of the present invention;

DETAILED DESCRIPTION OF EMBODIMENTS

Figure 1:
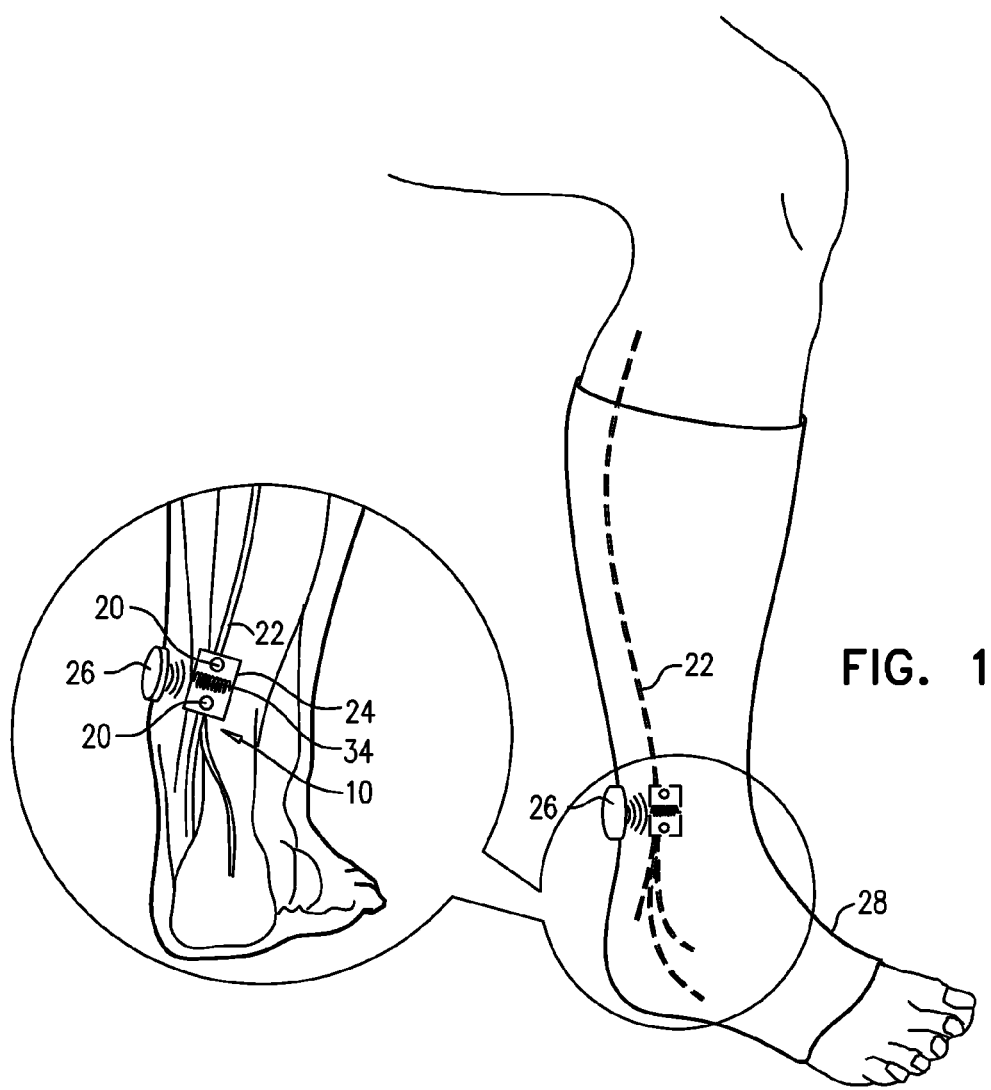
FIG. 1 is a schematic illustration of electrodes for stimulating the tibial nerve, in accordance with some applications of the present invention.

Reference is now made to FIG. 1, which is a schematic illustration of an implantable element 10 that includes electrodes 20 for stimulating a subject's tibial nerve 22, in accordance with some applications of the present invention. The electrodes are typically implanted in contact with the tibial nerve (e.g., by inserting the electrodes into the nerve, and/or by placing a housing 24 in contact with the nerve, the electrodes being disposed inside the housing). For some applications, the electrodes are implanted within 0.5 mm of the tibial nerve, e.g., within 0.3 mm of the tibial nerve. Alternatively, the electrodes are implanted at a distance of more than 0.5 mm, and/or less than 1 mm from the tibial nerve, e.g., within 0.5 mm to 1 mm from the tibial nerve. The electrodes are typically implanted on or near the tibial nerve, at a position in the vicinity of the subject's ankle. At this location, the tibial nerve is relatively close to the surface of the skin. Thus, in order to implant the electrodes at this location, it is typically not required to penetrate deeply into the subject's tissue. Typically, the electrodes are implanted in order to treat a subject who is identified as suffering from polyneuropathy.

Typically, electrodes 20 are disposed on a housing 24, at least a portion of which is flexible (e.g., a flexible silicone housing). The flexibility of the housing maintains contact between electrodes 20 and tibial nerve 22, even though the region of the subject's body in the vicinity of the implantation site undergoes significant motion. For some applications, the housing is an elongated silicone housing. Two electrodes are disposed inside the housing, there being gaps in the housing to provide contact of the electrodes with the tibial nerve. For some applications, a portion of the housing is not flexible, although most of the housing is flexible.

Typically, the disposition of electrodes 20 with respect to housing 24, and/or the shape of the housing is such that the current path of current from the electrodes, away from the tibial nerve is reduced. For example, the electrodes may be disposed on an inner surface of a housing that is placed around the tibial nerve, such that the housing directs the current flow toward the tibial nerve and reduces the current flow away from the tibial nerve.

For some applications, the housing is shaped as a cuff. For some applications, coupling elements (for example, a flexible hook (e.g., a silicone hook)), extend from housing 24 and are configured to couple the housing to the nerve, for example, in accordance with the techniques described hereinbelow. Alternatively or additionally, staples, a biological adhesive, and/or sutures are applied to the tibial nerve, and/or to tissue in the vicinity of the tibial nerve, in order to couple the housing to the nerve. Further alternatively or additionally, a mesh (e.g., a Dacron mesh) is disposed on an outer surface of the housing. The mesh causes fibrosis in the vicinity of the housing, thereby stabilizing the housing.

For some applications, electrodes 20 are disposed on a flexible coil that is placed around tibial nerve 22. The flexibility of the coil is typically such that the coil maintains contact between electrodes 20 and tibial nerve 22, even though the region of the subject's body in the vicinity of the implantation site undergoes significant motion. For some applications, the coil is placed around the tibial nerve in a minimally-invasive surgical procedure.

Electrodes 20 are actuated to drive a current into the tibial nerve by an external controller 26, which is external to the subject's body. For some applications, as shown in FIG. 1, the controller is coupled to a sock that is worn by the subject. Alternatively, the controller is placed in the vicinity of the electrodes, and outside the subject's body by alternative means, for example, by strapping external controller 26 to the subject's ankle, and/or by applying a patch to the subject's ankle, controller 26 being coupled to the patch. Further alternatively, controller 26 is coupled to housing 24, and is implanted in the vicinity of the tibial nerve.

Figure 2:
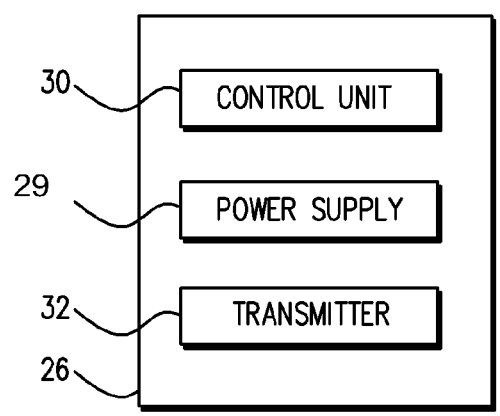
FIG. 2 is a block diagram of an external controller, in accordance with some applications of the present invention.

Reference is now made to FIG. 2, which is a block diagram of external controller 26, in accordance with some applications of the present invention. The external controller typically includes a power supply 29, a control unit 30, and a transmitter 32. In a typical application, the control unit wirelessly transmits a signal to implantable element 10, via the transmitter. An antenna 34 (shown in FIG. 1) of implantable element 10 receives the signal and relays the signal to the electrodes. The signal drives the electrodes to drive a current into the tibial nerve. The control unit typically comprises at least one power coupling element, a frequency down-converter, and at least one rectifier. For some applications, the control unit is configured to receive a signal, e.g., a myographic signal, and to actuate the electrodes responsively thereto.

The current that is driven into the tibial nerve typically has a frequency of more than 20 Hz, and/or less than 100 Hz (e.g., 20-100 Hz). For example, the frequency may be more than 30 Hz, and/or less than 80 Hz (e.g., 30-80 Hz), or more than 40 Hz, and/or less than 60 Hz (e.g., 40-60 Hz). The current typically has an amplitude of more than 0.2 mA, and/or less than 8 mA (e.g., 0.2-8 mA). For example, the amplitude may be more than 0.5 mA, and/or less than 4 mA (e.g., 0.5-4 mA). For some applications, for example, if the electrodes cannot be placed in close proximity to the tibial nerve, an amplitude of up to 10 mA is used.

For some applications, the location of the posterior tibial nerve is determined in accordance with the following procedure, and implantable element 10 is implanted based on the determined location. The skin of the subject is stimulated (typically electrically) at a distal site, e.g., on the sole of the foot. Nerve conduction signals along the tibial nerve that result from the stimulation are detected, in order to determine the location of the tibial nerve. Alternatively or additionally, sites in the subject's ankle are stimulated. In order to localize the tibial nerve, the response of a foot muscle (e.g., the abductor hallucis) of the subject to the stimulation at respective sites is recorded, typically, in accordance with nerve localization techniques that are known in the art.

Reference is now made to FIGS. 3A-B, which are schematic illustrations of housing 24 having rigid portions 23 and flexible portions 35 thereof. For some applications, as shown, the housing includes a plurality of portions, which are coupled to each other articulatably (i.e., in a manner that facilitates movement of the portions with respect to each other), typically via joints (as shown).

Typically, electronic control components (e.g., antenna 34, and/or another control component for receiving a signal from control unit 26) are disposed within a rigid seal (such as glass or metal) in one or more rigid portions. The electrodes are disposed on the flexible portions, such that contact between the electrodes and the tibial nerve is maintained due to the flexibility of the portion. For some applications, the flexible portions are made of a polymer and/or silicone. For some applications, the flexibility of the flexible portions is less than the flexibility provided by the joints, which couple the portions to each other. Typically, the flexible portions and/or the rigid portions are coupled to the tibial nerve in accordance with the techniques described herein.

For some applications, a single rigid portion is disposed at one end of the housing, as shown in FIG. 3A. Alternatively, a single rigid portion is disposed in a central region of the housing, as shown in FIG. 3B. Further alternatively, other combinations of flexible and rigid housing portions are used, as would be obvious to one skilled in the art, having read the specification of the present patent application.

Electrodes 20 are typically disposed on an inner surface of flexible portions of the housing. Alternatively, the electrodes are disposed at other positions on the housing. Typically, electrodes 20 are spaced at a distance of 8-10 mm from each other. Depending on the length of each of the flexible portions, a single electrode, or a plurality of electrodes are disposed on each of the flexible portions.

Figure 4A:
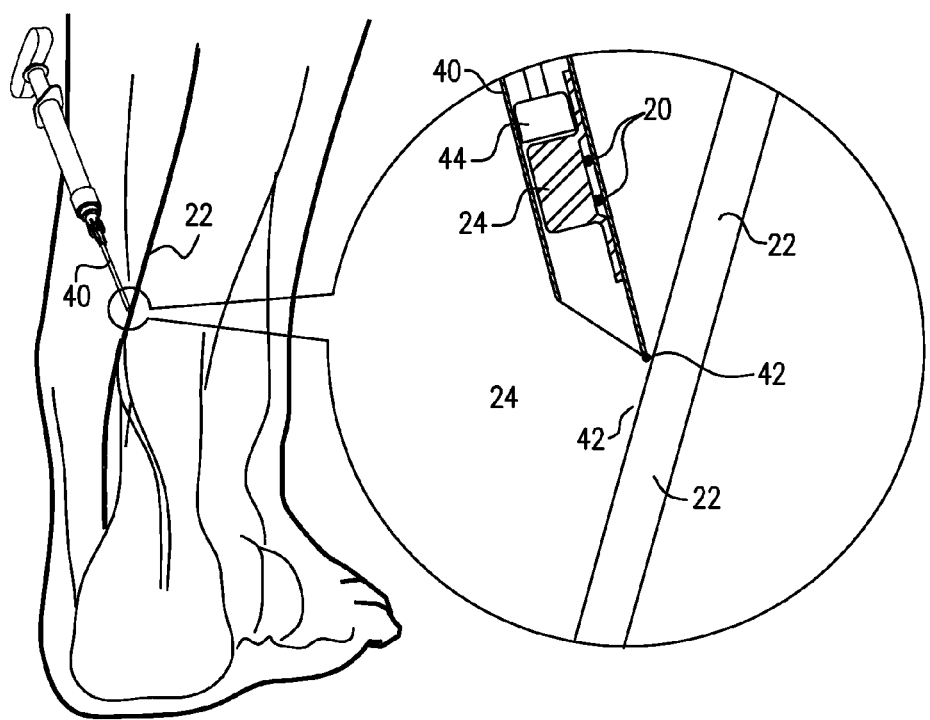
FIG. 4A is a schematic illustration of electrodes on a housing being injected into a subject's ankle to a vicinity of the tibial nerve, using an introducer, in accordance with some applications of the present invention.

Reference is now made to FIG. 4A, which is a schematic illustration of electrodes 20 on housing 24 being injected into the subject's ankle to a vicinity of tibial nerve 22, using an introducer 40, in accordance with some applications of the present invention. For some applications, at least one electrode 42 is disposed on the distal end of introducer 40 (as shown). Alternatively, at least one electrode 42 is disposed on the distal end of a dedicated electrode needle, the dedicated electrode needle being extendible from the distal end of introducer 40.

For some applications, electrodes 42 are stimulating electrodes. The electrodes are moved along the subject's tibial nerve and are used to stimulate the subject's tibial nerve. An implantation site for housing 24 is selected based upon the subject's response to the stimulation of the tibial nerve by electrodes 42, in accordance with the techniques described hereinabove. For some applications, a site of the tibial nerve is chosen as the implantation site, based upon the subject feeling pain relief when the stimulating electrodes stimulate the site.

Alternatively or additionally, electrodes 42 are sensing electrodes. The sensing electrodes are used to detect the location of the tibial nerve, and/or to determine a suitable implantation site for housing 24, by detecting action potentials. For example, the electrodes may detect action potentials generated in the tibial nerve in response to the subject's foot being electrically stimulated, in accordance with the techniques described hereinabove.

Figure 4B:
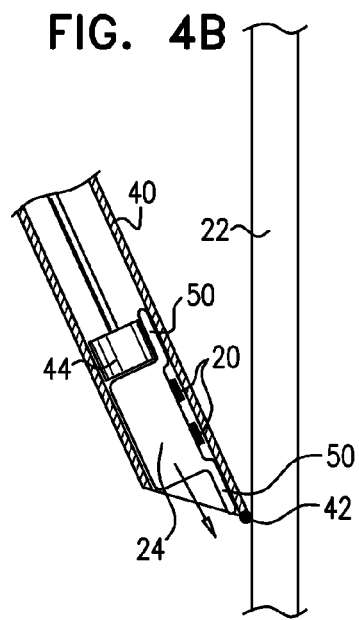
FIGS. 4B-D are schematic illustrations of respective steps of the housing being placed in the vicinity of the tibial nerve, in accordance with some applications of the present invention.
Figure 4C:
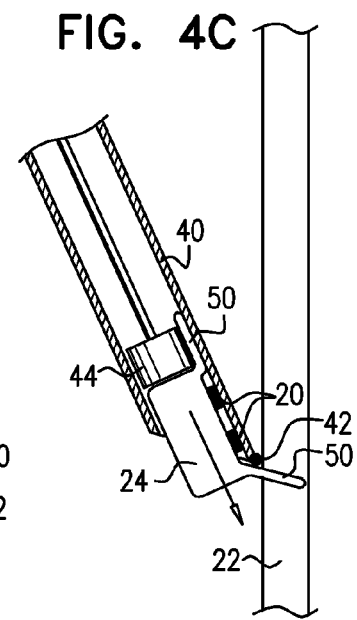
Figure 4D:
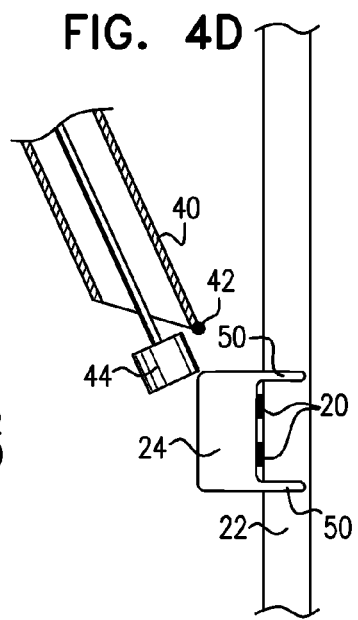

Reference is now made to FIGS. 4B-D, which are schematic illustrations of respective steps of housing 24 being injected to a vicinity of tibial nerve 22, in accordance with some applications of the present invention. For some applications, flexible coupling elements 50 are coupled to housing 24 and are disposed distally to the housing during injection of the housing into the subject's body, via introducer 40. For some applications, the coupling elements function as electrodes 20.

In a first step of the injection procedure, the distal end of introducer 40 is placed in the vicinity of tibial nerve 22, e.g., within 0.3 mm of the tibial nerve, such as within 0.5 mm (or within more than 0.5 mm, and/or less than 1 mm) of the tibial nerve. FIG. 4B shows the distal end of the introducer being placed in the vicinity of the tibial nerve. For some applications, the distal end of the introducer is positioned in response to stimulation and or sensing of electrodes 42, as described with reference to FIG. 4A.

Once the distal end of introducer 40 is suitably positioned, a pushing element 44 is used to push housing 24 distally, through introducer 40. Upon emerging from the distal end of the introducer, one or more distal coupling elements 50 curve outwards (FIG. 4C) and anchor themselves to tissue, for example, to tibial nerve 22 (FIG. 4C), or to tissue in the vicinity of the tibial nerve (e.g., within 0.3 mm of the tibial nerve, such as within 0.5 mm (or within more than 0.5 mm, and/or less than 1 mm) of the nerve).

Subsequent to the anchoring of distal coupling element 50 to the tissue, pushing element 44 continues to push housing 24 out of the distal end of introducer 40. When the proximal end of housing 24 emerges from the distal end of the introducer, proximal coupling element 50 couples the proximal end of the housing to the nerve, as shown in FIG. 4D.

Figure 4E:
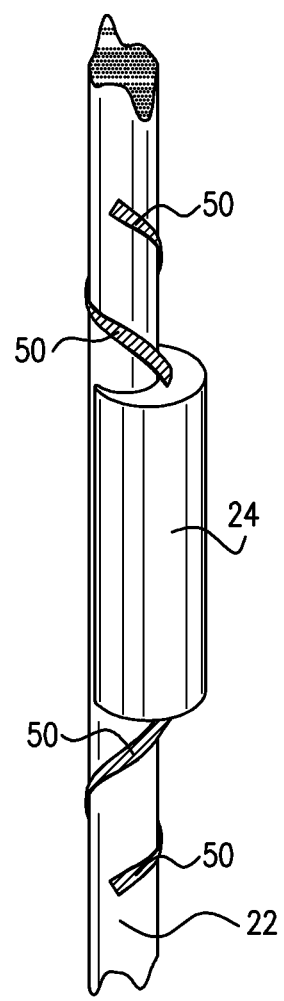
FIG. 4E is a schematic illustration of a housing having spiral coupling elements, in accordance with some applications of the present invention.

Reference is now made to FIG. 4E, which is a schematic illustration of housing 24 having spiral coupling elements 50, in accordance with some applications of the present invention. As shown, for some applications, the coupling elements are spirals, which couple housing 24 to the tibial nerve by curving around the tibial nerve. For some applications, the spiral coupling elements function as electrodes 20. Alternatively or additionally, electrodes 20 are disposed on the coupling elements and/or on housing 24.

Figure 5A:
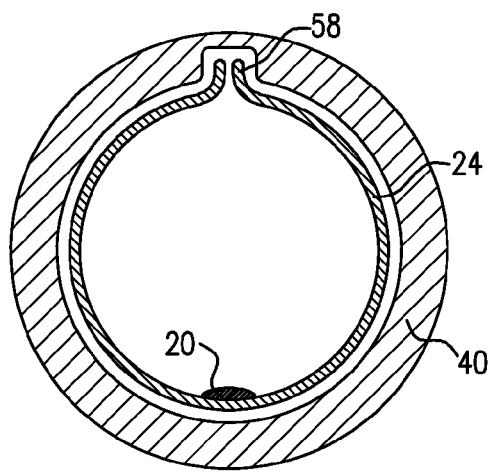
FIGS. 5A-B are schematic illustrations of a housing that is shaped to facilitate alignment of the housing with the tibial nerve, in accordance with some applications of the present invention.
Figure 5B:
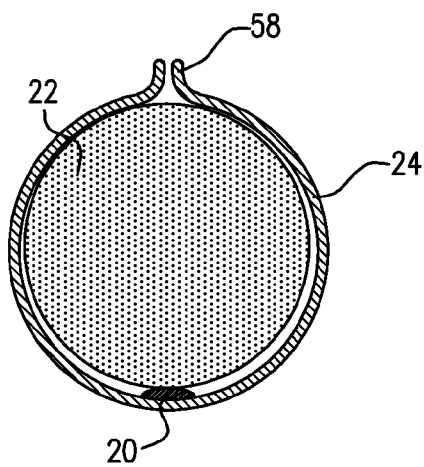

Reference is now made to FIGS. 5A-B, which are cross-sections of housing 24, shaped to facilitate alignment of the housing with the tibial nerve, in accordance with some applications of the present invention. FIG. 5A shows the housing during insertion of the housing into the subject's body, via introducer 40, and FIG. 5B shows the housing disposed on tibial nerve 22.

For some applications, a protrusion 58 protrudes from housing 24. Introducer 40 is shaped to define a lumen, a cross-section of which includes a groove that corresponds to the protrusion from the housing, as shown in FIG. 5A. Electrode 20 is coupled to the housing in a rotational position that is fixed with respect to the protrusion from the housing, for example, opposite the protrusion, as shown. Thus, during insertion of the housing into the subject's body and to the vicinity of the tibial nerve, the rotational location of the electrode with respect to the introducer may be controlled.

Typically, the introducer is oriented such that the electrode is placed in direct contact with the tibial nerve, as shown in FIG. 5B, or within 0.3 mm of the tibial nerve, such as within 0.5 mm (or within more than 0.5 mm, and/or less than 1 mm) of the nerve. Further typically, placing the electrode in direct contact with or within this distance of the tibial nerve reduces energy loss from the electrode, for example, relative to if the electrode were placed further from the tibial nerve. In addition, the shape of the injectable housing reduces the current path of current from the electrode, away from the tibial nerve.

Alternatively to the configuration of the apparatus shown in FIG. 5A, housing 24 is shaped to define a groove, and the introducer is shaped to define a lumen having a cross-section that includes a protrusion.

Figure 6A:
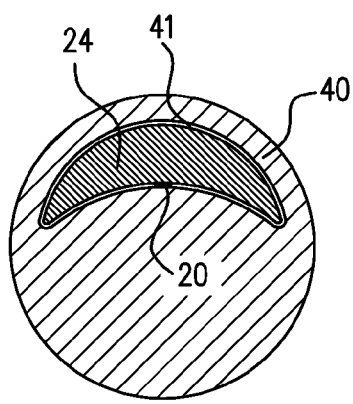
FIGS. 6A-B are schematic illustrations of a housing that is shaped to facilitate alignment of the housing with the tibial nerve, in accordance with some applications of the present invention.
Figure 6B:
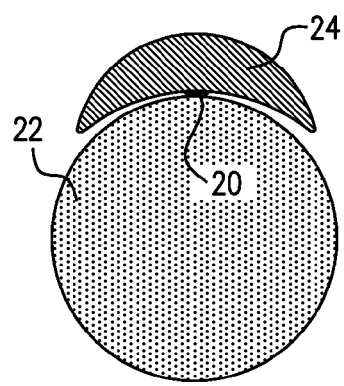

Reference is now made to FIGS. 6A-B, which are schematic illustrations of housing 24, shaped to facilitate alignment of the housing with tibial nerve 22, in accordance with some applications of the present invention. FIG. 6A shows the housing during insertion of the housing into the subject's body, via introducer 40, and FIG. 6B shows the housing disposed on tibial nerve 22.

For some applications, housing 24 has a non-circular cross-section. For example, the cross-section of the housing may be crescent shaped, as shown in FIGS. 6A-B. Introducer 40 is shaped to define a lumen 41 having a cross-section that corresponds to the shape of the cross-section of the housing, such that the housing can only be inserted through the lumen in a given rotational orientation. Electrode 20 is fixedly coupled to the housing. Thus, during insertion of the housing into the subject's body and to the vicinity of the tibial nerve, the rotational location of the electrode with respect to the introducer may be controlled. Typically, the introducer is oriented such that the electrode is placed in direct contact with the tibial nerve, as shown in FIG. 6B, or within 0.3 mm of the tibial nerve, such as within 0.5 mm (or within more than 0.5 mm, and/or less than 1 mm) of the nerve.

Figure 7A:
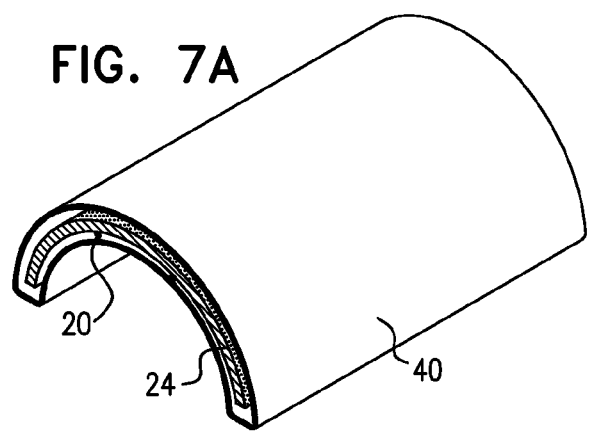
FIGS. 7A-C are schematic illustrations of a housing that undergoes a shape change, in accordance with some applications of the present invention.
Figure 7B:
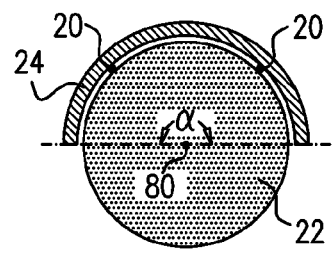
Figure 7C:
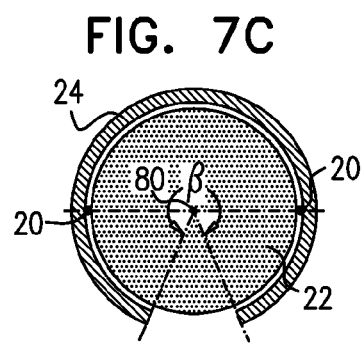

Reference is now made to FIGS. 7A-C, which are schematic illustrations of a housing 24 that undergoes a shape change, in accordance with some applications of the present invention. For some applications, housing 24 is placed on tibial nerve 22, while the housing has a first shape thereof. For example, FIG. 7A shows the housing in a first shape thereof inside introducer 40 (i.e., during insertion of the housing into the subject's body), and 7B shows the housing, in the first shape thereof, disposed on the tibial nerve. For some applications, while the housing is disposed around the tibial nerve in the first shape thereof, the housing defines an angle alpha around a longitudinal axis 80 of the tibial nerve of less than 180 degrees (as shown) or less, e.g., less than 90 degrees.

Typically, subsequent to the housing having been placed on or in the vicinity of the tibial nerve, the shape of the housing is changed to a second shape thereof. For example, the housing may comprise nitinol and/or another shape-change material, and the shape of the housing is changed by heating the housing. FIG. 7C shows the housing disposed around the tibial nerve in the second shape thereof. For some applications, while the housing is disposed around the tibial nerve in the second shape thereof, the housing defines an angle beta around longitudinal axis 80 of the tibial nerve of more than 180 degrees, e.g., 270 degrees or more.

Figure 8A:
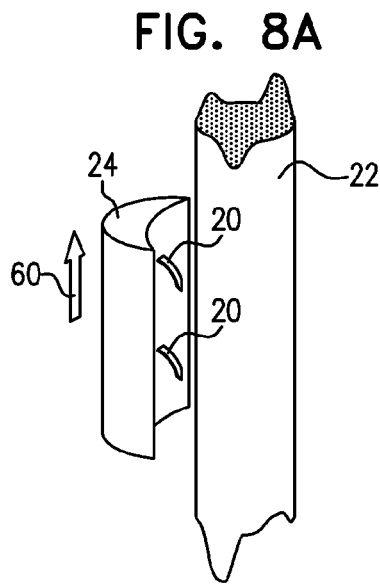
FIGS. 8A-B are schematic illustrations of electrodes being inserted into the tibial nerve, in accordance with some applications of the present invention.
Figure 8B:
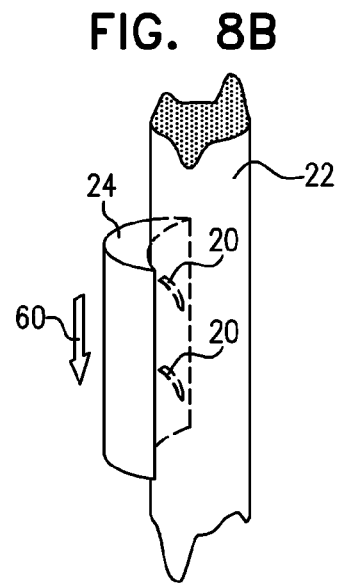

Reference is now made to FIGS. 8A-B, which are schematic illustrations of electrodes 20 that are configured to be inserted into the tibial nerve, in accordance with some applications of the present invention. Electrodes are disposed on housing 24, and are generally similar to electrodes 20 described hereinabove. During insertion of the electrodes to the vicinity of tibial nerve 22, housing 24 is advanced in the direction of arrow 60, such that even if the electrodes contact the tibial nerve, the electrodes slide past the tibial nerve, as shown in FIG. 8A. Subsequently, the housing is withdrawn in the direction of arrow 62. This causes electrodes 20 to become inserted into the tibial nerve, as shown in FIG. 8B.

Figure 9A:
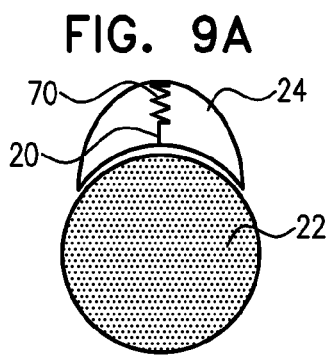
FIGS. 9A-B are schematic illustrations of electrodes being inserted into the tibial nerve, in accordance with some applications of the present invention.
Figure 9B:
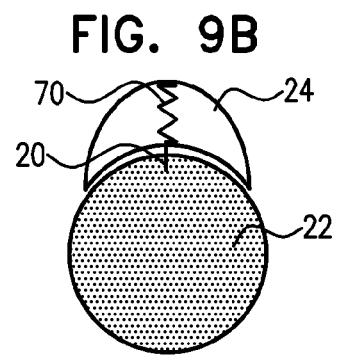

Reference is now made to FIGS. 9A-B, which are schematic illustration of electrodes 20 being inserted into tibial nerve 22, in accordance with some applications of the present invention. For some applications, electrodes 20 are needle electrodes. A spring 70 is disposed inside housing 24. Housing 24 is positioned adjacent to the tibial nerve while the spring is in a constricted configuration, as shown in FIG. 9A. When the housing is positioned at an implantation location of the housing, spring 70 is allowed to expand. Expansion of the spring pushes the needle electrodes into the tibial nerve.

For some applications, insertion of electrodes 20 into tibial nerve 22 in accordance with the techniques described with reference to FIGS. 8A-B and/or FIGS. 9A-B, anchors housing 24 to the tibial nerve. Alternatively or additionally, other techniques are used for anchoring the housing to the tibial nerve. For some applications, insertion of the electrodes into the tibial nerve maintains contact between the electrodes and the tibial nerve.

The inventors of the present application conducted an experiment in which EMG stimulating needle electrodes were inserted in close proximity to the tibial nerve of nine patients. In all of the patients, the electrode was placed in proximity to the tibial nerve on one side of the patient, and not in proximity to the tibial nerve of the other side of the patient. All of the patients suffered from a level of pain that was 2-9, based upon the following scale:

0-1: No pain
2-3: Mild pain
4-5: Discomforting—moderate pain
6-7: Distressing—severe pain
8-9: Intense—very severe pain
10: Unbearable pain Eight of the subjects were suffering from polyneuropathy, or neuropathic pain. One subject did not suffer from neuropathy, and may have been suffering from fibromyalgia. All patients were treated for 30 minute treatment sessions. Each treatment session was divided into five cycles of six minutes each, the cycles including five minutes of stimulation and a one minute pause. The patients were stimulated with a stimulating signal having an amplitude of 2-8 mA, and a frequency of 50 Hz.

All eight neuropathy patients, without exception, experienced marked alleviation of the neuropathic pain in the stimulated leg during stimulation. There was no beneficial effect on the patient who was not suffering from neuropathy, but was suffering from pain. In all of the neuropathic patients, the effect lasted after the stimulation ceased. In all of the neuropathic patients, the effect lasted for a total of at least three hours, and in one of the patients the effect lasted for five days.

Seven of the neuropathic patients had been treated with a wide range of anti-neuropathic pain medications, without significant improvement in their pain. These patients stated that tibial nerve stimulation was the only procedure that substantially improved their symptoms. One of the neuropathic patients had not received any medications, and the stimulation was the first treatment of her neuropathic pain. This patient experienced marked improvement of pain in both sides, although the improvement was more pronounced in the stimulated side.

In about half of the neuropathic patients, the beneficial effect of the stimulation (i.e., the pain relief) was bilateral, despite the stimulation having been applied to the tibial nerve of one side only. The inventors hypothesize that this is due to a spinal cord loop.

Based on the results of the aforementioned experiment, in accordance with some applications, the following treatment is applied to a subject who is identified as suffering from polyneuropathy. Implantable element 10 (shown in FIG. 1) is implanted in contact with or in the vicinity of the subject's tibial nerve, for example, in accordance with the techniques described hereinabove. External controller 26 (also shown in FIG. 1), or an implantable controller that is generally similar to external controller 26 is used to drive the electrodes to drive a current into the tibial nerve for a therapy period. For example, the therapy period may last more than 30 minutes, and/or or less than three hours. Alternatively, the therapy period may last more than two minutes, less than 10 minutes, and/or for a different period of time.

For some applications, therapy is administered to the subject once a day, several times (e.g., more than two, and/or less than eight times) a week or more, and/or in several therapy periods (e.g., more than two, and/or less than eight periods) over the course of a day. Typically, the length and/or frequency of the therapy periods is reduced, in response to the subject's condition improving. For some applications, therapy periods are applied on demand, based upon the subject feeling pain.

For some applications, the apparatus includes a lock-out mechanism to prevent the subject from applying the treatment for more than a maximal safe number of therapy periods over a given time period. During the therapy period the subject wears sock 28, or uses other means for keeping the external controller in the vicinity of the implantable element.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
    identifying a subject as suffering from polyneuropathy; and
    in response to the identifying:
        placing electrodes in contact with a portion of the subject's body within 1 mm of a tibial nerve of the subject, the electrodes being disposed on a housing that includes flexible and rigid portions thereof, the portions being articulatably coupled to each other via a joint of the housing that is more flexible than the flexible portion such as to maintain contact between the electrodes and the portion of the subject's body by the housing articulating; and
        driving the electrodes to treat the polyneuropathy by driving a current into the tibial nerve.

2. The method according to claim 1, wherein placing the electrodes comprises:
    when the electrodes are driven to drive the current into the tibial nerve,
    reducing a current path from the electrodes away from the tibial nerve, using the housing, by
    placing the electrodes within 1 mm of the tibial nerve, in a given configuration with respect to the housing.

3. The method according to claim 1, further comprising detecting a myographic signal of the subject, wherein driving the electrodes comprises driving the electrodes responsively to the myographic signal.

4. The method according to claim 1, further comprising, subsequent to placing the electrodes within 1 mm of the tibial nerve of the subject, coupling the housing to the tibial nerve by changing a shape of the housing.

5. The method according to claim 1, wherein placing the electrodes within 1 mm of the tibial nerve of the subject comprises placing the electrodes in contact with the tibial nerve.

6. The method according to claim 1, wherein placing the electrodes comprises placing the electrodes within 0.3 mm of the tibial nerve.

7. The method according to claim 1, wherein driving the electrodes to drive the current comprises driving the electrodes to drive a current having a frequency of 20 Hz to 60 Hz.

8. The method according to claim 1, wherein driving the electrodes to drive the current comprises driving the electrodes to drive the current for a therapy period having a duration of between two minutes and ten minutes.

9. The method according to claim 8, wherein driving the electrodes to drive the current for the therapy period comprises driving the electrodes to drive the current during 2-8 therapy periods per day.

10. The method according to claim 8, wherein driving the electrodes to drive the current for the therapy period comprises driving the electrodes to drive the current during 2-8 therapy periods per week.

11. The method according to claim 1, wherein driving the electrodes to drive the current comprises driving the electrodes to drive a current having an amplitude of between 0.5 mA and 8 mA.

12. The method according to claim 1, wherein placing electrodes within 1 mm of the tibial nerve of the subject comprises inserting the electrodes into the tibial nerve.

13. The method according to claim 1, wherein placing the electrodes disposed on the housing that includes flexible and rigid portions thereof comprises placing the electrodes disposed on a housing that includes flexible and rigid portions thereof, the rigid portion including a control component that is configured to receive a signal from a control unit that is disposed outside the subject's body.

14. The method according to claim 1, wherein the flexible and rigid portions of the housing have respective crescent-shaped cross sections, and wherein placing the electrodes comprises placing the electrodes, such that each of the flexible and rigid portions is disposed at least partway around the tibial nerve.

15. The method according to claim 1, wherein:
    the flexible portion of the housing includes a first flexible portion, articulatably coupled at a first end thereof to the rigid portion via the joint, and the apparatus further includes a second flexible portion, articulatably coupled to a second end of the first flexible portion via another joint that is more flexible than the first flexible portion and the second flexible portion, and
    placing the electrodes comprises placing the electrodes disposed on the housing that includes the first flexible portion that is articulatably coupled to the rigid portion and to the second flexible portion via the joints.

16. The method according to claim 1, wherein placing the electrodes comprises injecting the flexible and rigid portions into the subject via an introducer.

17. The method according to claim 16, wherein placing the electrodes comprises coupling the housing to the nerve while at least part of the housing is disposed within the introducer, and subsequently pushing at least the part of the housing out of the introducer.

18. Apparatus for treating polyneuropathy of a subject, comprising:
    one or more electrodes configured to be placed in contact with a portion of the subject's body within 1 mm of a tibial nerve of the subject;
    a housing that is at least partially flexible, the housing comprising flexible and rigid portions thereof, the portions being articulatably coupled to each other via a joint of the housing that is more flexible than the flexible portion, the housing being configured to support the electrodes and to maintain contact between the electrodes and the portion of the subject's body by articulating; and a control unit configured to be placed outside a body of the subject, and to drive the electrodes to treat the polyneuropathy by driving a current into the tibial nerve.

19. The apparatus according to claim 18, wherein the housing comprises a shape-change material, and wherein the housing is configured to maintain contact between the electrodes and the portion of the subject's body by changing a shape of the housing.

20. The apparatus according to claim 18, wherein the housing is configured to reduce a current path from the electrodes away from the tibial nerve.

21. The apparatus according to claim 18, wherein the electrodes are configured to be placed in contact with the tibial nerve.

22. The apparatus according to claim 18, further comprising an implantable control component configured to receive a signal from the control unit, wherein the implantable control component is disposed within the rigid portion of the housing, and the electrodes are disposed within the flexible portion of the housing.

23. The apparatus according to claim 18, wherein the electrodes are configured to be inserted into the tibial nerve.

24. The apparatus according to claim 23, further comprising one or more springs coupled to the one or more electrodes and configured to insert the electrodes into the tibial nerve by expanding.

25. The apparatus according to claim 18, further comprising an introducer, wherein the electrodes are configured to be placed in contact with the subject's tibial nerve by the housing being injected to a vicinity of the tibial nerve via the introducer.

26. The apparatus according to claim 18, wherein the one or more electrodes are configured to be placed in contact with a portion of the subject's body within 0.3 mm of the tibial nerve.

27. The apparatus according to claim 18, wherein the flexible and rigid portions of the housing have respective crescent-shaped cross sections configured to facilitate placement of the flexible and rigid portions at least partway around the tibial nerve.

28. The apparatus according to claim 18, wherein the flexible portion of the housing comprises a first flexible portion, articulatably coupled at a first end thereof to the rigid portion via the joint, and the apparatus further comprises a second flexible portion, articulatably coupled to a second end of the first flexible portion via another joint that is more flexible than the first flexible portion and the second flexible portion.

29. The apparatus according to claim 18, further comprising an introducer, wherein the introducer and the housing are configured such that the flexible and rigid portions are injectable into the subject via the introducer.

30. The apparatus according to claim 29, further comprising a pushing element, wherein (1) the housing is configured to be coupled to the nerve of the subject while at least part of the housing is disposed within the introducer, and (2) the introducer and the housing are configured to facilitate pushing, by the pushing element, of at least the part of the housing out of the introducer subsequently to the coupling of the housing to the nerve.

* * * * *